(12) United States Patent
Herbst et al.

(10) Patent No.: US 10,777,059 B2
(45) Date of Patent: *Sep. 15, 2020

(54) ALERT MANAGEMENT UTILIZING MOBILE DEVICES

(71) Applicant: CERNER INNOVATION, INC., Kansas City, KS (US)

(72) Inventors: Damon Herbst, Shawnee, KS (US); Cassie Lyn Bahr, Prairie Village, KS (US); Rajneesh Mehra, Overland Park, KS (US); Jamie Brothers, Lee's Summit, MO (US); Jay Christopher Vaglio, Kansas City, KS (US); Matt Ryan Anderson, Kansas City, MO (US)

(73) Assignee: CERNER INNOVATION, INC., Kansas City, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 16/743,029

(22) Filed: Jan. 15, 2020

(65) Prior Publication Data
US 2020/0152038 A1    May 14, 2020

Related U.S. Application Data

(60) Continuation of application No. 16/179,096, filed on Nov. 2, 2018, now Pat. No. 10,580,279, which is a
(Continued)

(51) Int. Cl.
*G08B 21/02*  (2006.01)
*G16H 80/00*  (2018.01)
(Continued)

(52) U.S. Cl.
CPC .......... *G08B 21/02* (2013.01); *G06F 3/0482* (2013.01); *G08B 25/016* (2013.01);
(Continued)

(58) Field of Classification Search
CPC ...................................................... G08B 21/02
See application file for complete search history.

(56) References Cited

U.S. PATENT DOCUMENTS 1,039,713 A    10/1912   Eaton
4,237,344 A    12/1980   Moore
(Continued)

OTHER PUBLICATIONS

"Arc Solutions and Extension, Inc. Announce New Collaboration Software Solutions, Specifically Designed for the Healthcare Sector", Press Release by Extension Healthcare, Jan. 7, 2010, 2 pages.
(Continued)

*Primary Examiner* — Travis R Hunnings
(74) *Attorney, Agent, or Firm* — Shook, Hardy & Bacon, L.L.P.

(57) ABSTRACT

Methods, computer systems, and computer-storage medium are provided for managing patient alerts using a mobile device. A mobile device associated with a patient caregiver receives a critical alert related to the patient, and the alert is presented on the mobile device. The alert includes important contextual information that enables the caregiver to make a quick assessment of how to effectively address the alert. The alert includes options for accepting the alert or rejecting the alert. Acceptance of the alert enables the caregiver to communicate the alert to selected caregivers that can assist in managing the alert. Rejecting the alert causes the alert to be automatically communicated to additional caregivers associated with patient.

20 Claims, 9 Drawing Sheets

Related U.S. Application Data continuation of application No. 15/873,158, filed on Jan. 17, 2018, now Pat. No. 10,121,346, which is a continuation of application No. 15/684,563, filed on Aug. 23, 2017, now Pat. No. 9,911,300, which is a division of application No. 15/630,617, filed on Jun. 22, 2017, now Pat. No. 9,836,940, which is a continuation of application No. 15/392,926, filed on Dec. 28, 2016, now Pat. No. 9,805,573, which is a continuation of application No. 14/877,808, filed on Oct. 7, 2015, now Pat. No. 9,582,978, which is a continuation of application No. 13/731,191, filed on Dec. 31, 2012, now Pat. No. 9,185,202.

(51) Int. Cl.
| | |
|---|---|
| *H04M 19/04* | (2006.01) |
| *G08B 25/01* | (2006.01) |
| *G08B 27/00* | (2006.01) |
| *H04M 1/725* | (2006.01) |
| *G16H 40/20* | (2018.01) |
| *G06F 3/0482* | (2013.01) |
| *H04W 4/12* | (2009.01) |
| *G16H 50/50* | (2018.01) |
| *G16H 40/67* | (2018.01) |
| *G16H 10/60* | (2018.01) |
| *G16H 15/00* | (2018.01) |
| *G16H 50/30* | (2018.01) |

(52) U.S. Cl.
CPC .......... *G08B 27/006* (2013.01); *G16H 10/60* (2018.01); *G16H 15/00* (2018.01); *G16H 40/20* (2018.01); *G16H 40/67* (2018.01); *G16H 50/30* (2018.01); *G16H 50/50* (2018.01); *G16H 80/00* (2018.01); *H04M 1/72541* (2013.01); *H04M 19/04* (2013.01); *H04W 4/12* (2013.01)

(56) References Cited

U.S. PATENT DOCUMENTS

| | | | |
|---|---|---|---|
| 5,319,355 | A | 6/1994 | Russek |
| 5,319,363 | A | 6/1994 | Welch et al. |
| 5,534,851 | A | 7/1996 | Russek |
| 5,942,986 | A | 8/1999 | Shabot et al. |
| 5,999,846 | A | 12/1999 | Pardey et al. |
| 6,754,516 | B2 | 6/2004 | Mannheimer |
| 6,804,656 | B1 | 10/2004 | Rosenfeld et al. |
| 6,928,370 | B2 | 8/2005 | Anuzis et al. |
| 7,035,622 | B2 | 4/2006 | Pappalardo et al. |
| 7,035,623 | B2 | 4/2006 | Pappalardo et al. |
| 7,090,053 | B2 | 8/2006 | Bothwell et al. |
| 7,123,950 | B2 | 10/2006 | Mannheimer |
| 7,215,945 | B2 | 5/2007 | Pappalardo et al. |
| 7,224,281 | B2 | 5/2007 | Santoso et al. |
| 7,225,408 | B2 | 5/2007 | O'Rourke |
| 7,249,036 | B2 | 7/2007 | Bayne |
| 7,256,708 | B2 | 8/2007 | Rosenfeld et al. |
| 7,307,543 | B2 | 12/2007 | Rosenfeld et al. |
| 7,315,825 | B2 | 1/2008 | Rosenfeld et al. |
| 7,321,862 | B2 | 1/2008 | Rosenfeld et al. |
| D577,734 | S | 9/2008 | Ryu et al. |
| 7,430,692 | B2 | 9/2008 | Whit et al. |
| 7,454,359 | B2 | 11/2008 | Rosenfeld et al. |
| 7,475,019 | B2 | 1/2009 | Rosenfeld et al. |
| D599,812 | S | 9/2009 | Hirsch |
| D599,813 | S | 9/2009 | Hirsch |
| D607,004 | S | 12/2009 | Kordus et al. |
| D625,317 | S | 10/2010 | Jewitt et al. |
| D631,891 | S | 2/2011 | Vance et al. |
| D640,276 | S | 6/2011 | Woo |
| 7,981,032 | B2 | 7/2011 | Santoso et al. |
| 8,015,030 | B2 | 9/2011 | Brown |
| 3,100,829 | A1 | 1/2012 | Rothman et al. |
| 8,092,380 | B2 | 1/2012 | Rothman et al. |
| 8,122,006 | B2 | 2/2012 | de Castro Alves et al. |
| 8,160,895 | B2 | 4/2012 | Schmitt et al. |
| 8,165,893 | B1 | 4/2012 | Goldberg et al. |
| 8,170,887 | B2 | 5/2012 | Rosenfeld et al. |
| 8,175,895 | B2 | 5/2012 | Rosenfeld et al. |
| D662,507 | S | 6/2012 | Mori et al. |
| D665,399 | S | 8/2012 | Carpenter et al. |
| 8,332,017 | B2 | 12/2012 | Tarassenko et al. |
| 8,355,925 | B2 | 1/2013 | Rothman et al. |
| 8,374,988 | B2 | 2/2013 | Gawlick |
| 8,401,606 | B2 | 3/2013 | Mannheimer |
| 8,401,607 | B2 | 3/2013 | Mannheimer |
| 8,403,847 | B2 | 3/2013 | Rothman et al. |
| 8,416,085 | B2 | 4/2013 | Gawlick |
| 8,417,233 | B2 | 4/2013 | Woloshyn |
| 8,417,662 | B2 | 4/2013 | Gawlick |
| D682,294 | S | 5/2013 | Kanalakis, Jr. et al. |
| D682,844 | S | 5/2013 | Friedlander et al. |
| D682,858 | S | 5/2013 | Frijlink |
| 8,451,101 | B2 | 5/2013 | Somasundaram et al. |
| 8,454,506 | B2 | 6/2013 | Rothman et al. |
| D686,221 | S | 7/2013 | Brinda et al. |
| 8,543,534 | B2 | 9/2013 | Alves et al. |
| D695,773 | S | 12/2013 | Tagliabue et al. |
| D696,682 | S | 12/2013 | Kim et al. |
| 8,615,291 | B2 | 12/2013 | Moorman et al. |
| D700,914 | S | 3/2014 | Jin et al. |
| D701,221 | S | 3/2014 | Ahmed et al. |
| D705,239 | S | 5/2014 | Thompson et al. |
| 8,775,196 | B2 | 7/2014 | Simpson et al. |
| 8,838,196 | B2 | 9/2014 | Mannheimer |
| 8,842,001 | B2 | 9/2014 | Gilham et al. |
| D714,817 | S | 10/2014 | Lee |
| D715,820 | S | 10/2014 | Rebstock |
| D717,808 | S | 11/2014 | Tsuru et al. |
| 8,886,663 | B2 | 11/2014 | Gainsboro et al. |
| 8,886,792 | B2 | 11/2014 | Biondi et al. |
| D719,577 | S | 12/2014 | Tsuru et al. |
| D720,766 | S | 1/2015 | Mandal et al. |
| 8,948,734 | B2 | 2/2015 | Vaglio et al. |
| D733,175 | S | 6/2015 | Bae |
| 9,052,809 | B2 | 6/2015 | Vesto |
| D734,349 | S | 7/2015 | Amin et al. |
| D734,350 | S | 7/2015 | Inose et al. |
| D736,789 | S | 8/2015 | Tursi et al. |
| 9,159,313 | B2 | 10/2015 | Saeki et al. |
| D742,909 | S | 11/2015 | Lee et al. |
| 9,185,202 | B2 * | 11/2015 | Herbst .................. G16H 15/00 |
| D747,343 | S | 1/2016 | Brinda et al. |
| D751,097 | S | 3/2016 | Sarafa et al. |
| D752,604 | S | 3/2016 | Zhang |
| D752,614 | S | 3/2016 | Kwon et al. |
| 9,280,637 | B2 | 3/2016 | Vaglio et al. |
| D753,165 | S | 4/2016 | Watson |
| D753,707 | S | 4/2016 | Yang |
| D754,176 | S | 4/2016 | Kim |
| D757,771 | S | 5/2016 | Drozd et al. |
| D757,778 | S | 5/2016 | Lemay |
| D758,386 | S | 6/2016 | Zhang |
| D758,400 | S | 6/2016 | Chang et al. |
| D759,687 | S | 6/2016 | Chang et al. |
| D760,738 | S | 7/2016 | Scalisi et al. |
| 9,400,874 | B2 | 7/2016 | Powell et al. |
| D762,676 | S | 8/2016 | Lim |
| D763,290 | S | 8/2016 | Gupta et al. |
| D763,881 | S | 8/2016 | Smith et al. |
| D763,882 | S | 8/2016 | Liang |
| D764,511 | S | 8/2016 | Han et al. |
| D765,110 | S | 8/2016 | Liang |
| D766,294 | S | 9/2016 | Smith |
| D767,605 | S | 9/2016 | Mensinger et al. |
| 9,449,355 | B2 | 9/2016 | Kozicki et al. |
| D770,491 | S | 11/2016 | Jung |
| D771,667 | S | 11/2016 | Woo |
| D771,670 | S | 11/2016 | Chan et al. |
| D772,259 | S | 11/2016 | Pahwa et al. |

(56) References Cited

U.S. PATENT DOCUMENTS

| | | | |
|---|---|---|---|
| D775,167 S | 12/2016 | Vazquez | |
| D777,184 S | 1/2017 | Yang et al. | |
| D777,758 S | 1/2017 | Kisselev et al. | |
| D778,929 S | 2/2017 | Mensinger et al. | |
| D779,517 S | 2/2017 | Pierson et al. | |
| D780,191 S | 2/2017 | Kelley | |
| 9,582,978 B2* | 2/2017 | Herbst | G06F 3/0482 |
| D781,315 S | 3/2017 | Wang | |
| D784,384 S | 4/2017 | Hong et al. | |
| D785,003 S | 4/2017 | Yun et al. | |
| D785,008 S | 4/2017 | Lim et al. | |
| D785,009 S | 4/2017 | Lim et al. | |
| D785,012 S | 4/2017 | Jou | |
| D785,029 S | 4/2017 | Gedrich et al. | |
| 9,626,479 B2 | 4/2017 | Zaleski | |
| 9,659,482 B2 | 5/2017 | Yang et al. | |
| D789,947 S | 6/2017 | Sun | |
| D789,949 S | 6/2017 | Sun | |
| 9,706,966 B2 | 7/2017 | Colman et al. | |
| 9,747,778 B2 | 8/2017 | Mukherji et al. | |
| D801,373 S | 10/2017 | Vaglio et al. | |
| 9,805,573 B2* | 10/2017 | Herbst | G16H 10/60 |
| 9,836,940 B2* | 12/2017 | Herbst | G16H 50/30 |
| 9,881,475 B2* | 1/2018 | Herbst | G16H 50/50 |
| 9,911,300 B2* | 3/2018 | Herbst | H04M 1/72541 |
| 9,924,908 B2 | 3/2018 | Hubert et al. | |
| 10,121,346 B2 | 11/2018 | Herbst et al. | |
| 10,580,279 B2* | 3/2020 | Herbst | G08B 27/006 |
| 2002/0040282 A1 | 4/2002 | Bailey et al. | |
| 2002/0062230 A1 | 5/2002 | Morag et al. | |
| 2003/0163789 A1 | 8/2003 | Blomquist | |
| 2003/0191730 A1 | 10/2003 | Adkins et al. | |
| 2004/0073453 A1 | 4/2004 | Nenov et al. | |
| 2004/0172222 A1* | 9/2004 | Simpson | G06F 19/3418 702/189 |
| 2005/0065817 A1* | 3/2005 | Mihai | A61B 5/0002 705/2 |
| 2005/0146431 A1 | 7/2005 | Hastings et al. | |
| 2005/0151640 A1 | 7/2005 | Hastings | |
| 2006/0049936 A1 | 3/2006 | Collins et al. | |
| 2006/0161457 A1 | 7/2006 | Rapaport et al. | |
| 2007/0239488 A1 | 10/2007 | Derosso | |
| 2008/0021709 A1 | 1/2008 | Greer | |
| 2008/0027288 A1 | 1/2008 | Renz | |
| 2008/0074951 A1 | 3/2008 | Hubicki | |
| 2009/0048868 A1 | 2/2009 | Portnoy et al. | |
| 2010/0001838 A1 | 1/2010 | Miodownik et al. | |
| 2010/0123587 A1 | 5/2010 | Walls | |
| 2010/0137693 A1 | 6/2010 | Porras et al. | |
| 2010/0223071 A1 | 9/2010 | Kland et al. | |
| 2011/0001605 A1 | 1/2011 | Kiani et al. | |
| 2011/0054946 A1 | 3/2011 | Coulter et al. | |
| 2011/0105979 A1 | 5/2011 | Schlaeper et al. | |
| 2011/0106560 A1* | 5/2011 | Eaton, Jr. | G01C 21/20 705/3 |
| 2011/0196306 A1 | 8/2011 | De La Huerga | |
| 2011/0208816 A1 | 8/2011 | Chavez | |
| 2011/0276396 A1 | 11/2011 | Rathod | |
| 2011/0295621 A1 | 12/2011 | Farooq et al. | |
| 2012/0075103 A1 | 3/2012 | Powell et al. | |
| 2012/0101847 A1 | 4/2012 | Johnson et al. | |
| 2012/0169467 A1 | 7/2012 | Condra | |
| 2012/0278104 A1 | 11/2012 | Traughber et al. | |
| 2012/0284040 A1 | 11/2012 | Dupin | |
| 2013/0009783 A1 | 1/2013 | Tran | |
| 2013/0049950 A1* | 2/2013 | Wohlert | H04M 11/04 340/531 |
| 2013/0065569 A1 | 3/2013 | Leipzig et al. | |
| 2013/0085765 A1 | 4/2013 | Tuchinda et al. | |
| 2013/0085798 A1 | 4/2013 | Spatola et al. | |
| 2013/0096953 A1 | 4/2013 | Beverly et al. | |
| 2013/0103768 A1 | 4/2013 | Freebeck | |
| 2013/0104077 A1 | 4/2013 | Felt | |
| 2013/0162424 A1 | 6/2013 | Treacy | |
| 2013/0183923 A1 | 7/2013 | Brackett et al. | |
| 2013/0297348 A1 | 11/2013 | Cardoza et al. | |
| 2014/0039351 A1* | 2/2014 | Mix | A61B 5/1114 600/587 |
| 2014/0051399 A1 | 2/2014 | Walker et al. | |
| 2014/0070939 A1 | 3/2014 | Halverson et al. | |
| 2014/0085080 A1 | 3/2014 | Carnes | |
| 2014/0097961 A1 | 4/2014 | Vaglio et al. | |
| 2014/0099929 A1 | 4/2014 | Vaglio et al. | |
| 2014/0100873 A1 | 4/2014 | Vaglio et al. | |
| 2014/0132413 A1 | 5/2014 | Fox et al. | |
| 2014/0172996 A1 | 6/2014 | Deeter et al. | |
| 2014/0184408 A1 | 7/2014 | Herbst et al. | |
| 2014/0337442 A1 | 11/2014 | Zhuang et al. | |
| 2014/0358585 A1 | 12/2014 | Reiner | |
| 2015/0081339 A1 | 3/2015 | Vaglio et al. | |
| 2015/0137968 A1 | 5/2015 | Rusin et al. | |
| 2015/0148617 A1 | 5/2015 | Friedman | |
| 2015/0254957 A1 | 9/2015 | Wilson et al. | |
| 2016/0027277 A1 | 1/2016 | Herbst et al. | |
| 2016/0110040 A1 | 4/2016 | Vaglio et al. | |
| 2016/0360160 A1 | 12/2016 | Eizenberg | |
| 2017/0024091 A1 | 1/2017 | Hosier, Jr. | |
| 2017/0098037 A1 | 4/2017 | Agassi et al. | |
| 2017/0109018 A1 | 4/2017 | Vaglio et al. | |
| 2017/0193801 A1 | 7/2017 | Bala et al. | |
| 2017/0265819 A1 | 9/2017 | Colman et al. | |
| 2018/0110477 A1 | 4/2018 | Collins et al. | |
| 2018/0153455 A1 | 6/2018 | Guazzi et al. | |
| 2018/0315428 A1 | 11/2018 | Johnson et al. | |
| 2019/0066841 A1 | 2/2019 | Bala et al. | |
| 2019/0244506 A1 | 8/2019 | Herbst et al. | |
| 2019/0294318 A1 | 9/2019 | Vaglio et al. | |

OTHER PUBLICATIONS

Armasu, Lucian, "Contactive—A Caller ID App that Showcases Android's Openess", TechDomino, Available online at: <http://techdomino.com/contactive-a-caller-id-app-that-showcases-androids-openess/>, Retrieved on May 3, 2017, pp. 1-3.

"Clinical Workflow Solutions, Extension® HealthAlert™", Brochure published by NEC Corporation of America, 2012, 8 pages.

Detraz, Jerome, "Find and Replace Pop-Up Window", Sketchappsource.com, Available online at: <https://web.archive.org/web/20130717090053/https://www.sketchappsources.com/free-source/190-find-replace-pop-up-window.html>, Retrieved on Jul. 3, 2017, pp. 1-2.

"ExDialer Dialer & Contacts", Modoohut Communication, Android Apps on Google Play, Available online at<https://play.google.com/store/apps/details?id=com.modoohut.dialer&hl=en>, Retrieved on May 3, 2017, pp. 1-3.

"Extension, Inc. and AeroScout Partner to Deliver Solutions for Healthcare RTLS and VoIP", Healthcare, Feb. 19, 2010, 2 pages.

"Extension, Inc. Launches New Interactive Communications Solution", Healthcare, Available online at: <http://www.extensionhealthcare.com/news-events/press-releases/press-release-archive/extension-inc-launches-new-interactive-communications-solution/>, May 25, 2011, pp. 1-3.

"Extension Mobile for Enterprise Healthcare Organizations Now Available on Apple iPhone and iPod Touch Via Apple AppStore", Healthcare, Jan. 10, 2011, 2 pages.

"How to Create a Cool and Usable CSS3 Search Box", catalin.red, Available online at: <https://catalin.red/how-to-create-a-cool-and-usable-css3-search-box/>, Feb. 18, 2011, pp. 1-2.

"How to Download Skype app on Android and do Voice and Video Chat", Howtoconnect, Available online at: <http://www.howto-connect.com/how-to-download-skype-app-on-android-and-do-voice-and-video-chat/>, Oct. 29, 2012, pp. 1-5.

Manager, "How to Set Up Zoom on Android", Recovery Android, Available online at: <http://blog.recovery-android.com/set-up-zoom-in-android/>, Jan. 14, 2016, pp. 1-3.

"Review: Our Favourite Effective Contact Managers", Best Contact Manager Applications Review, Contaker Blog, Available online at: <http://blog.contaker.com/?p=61>, Retrieved on May 3, 2017, pp. 1-6.

(56) References Cited

OTHER PUBLICATIONS

Riano et al., "MPM: A Knowledge-Based Functional Model of Medical Practice", Journal of Biomedical Informatics, vol. 46, No. 3, 2013, pp. 379-387.
Simon NG, "How to Add Search Bar in Table View", appcoda.com, Available online at: <https://www.appcoda.com/how-to-add-search-bar-uitableview/>, Jul. 8, 2012, pp. 1-5.
"The American Hospital Association Endorses the Extension Healthid Smart Card System", News Medical Life Sciences, Aug. 21, 2009, 2 pages.
Thomas, Tony, "How to Design an iPhone App in Photoshop", Medialoot.com, Available online at: <https://medialoot.com/blog/how-to-design-an-iphone-app-in-photoshop/>, Oct. 26, 2011, 23 pages.

* cited by examiner

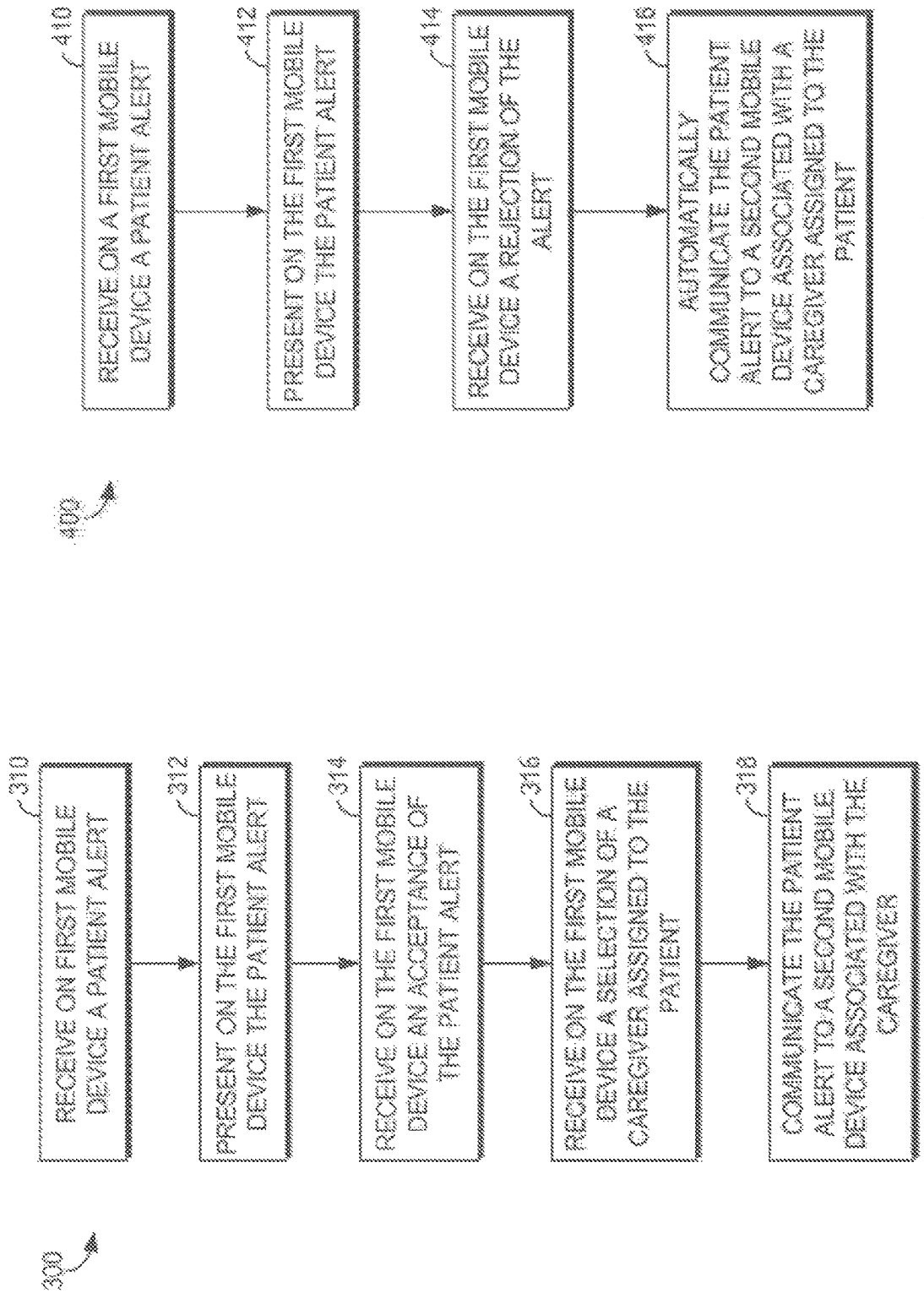

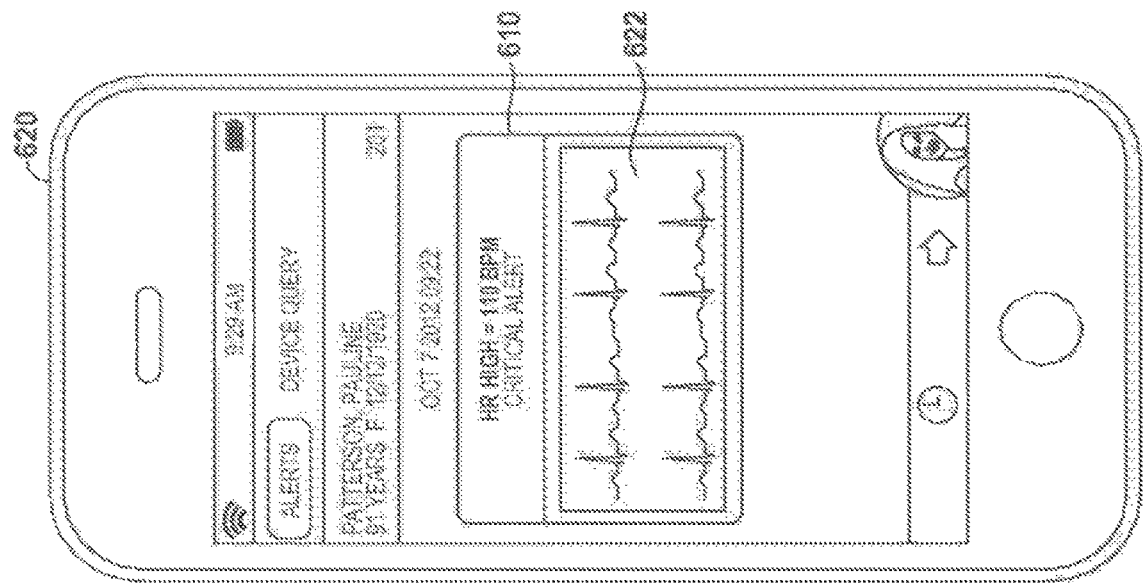
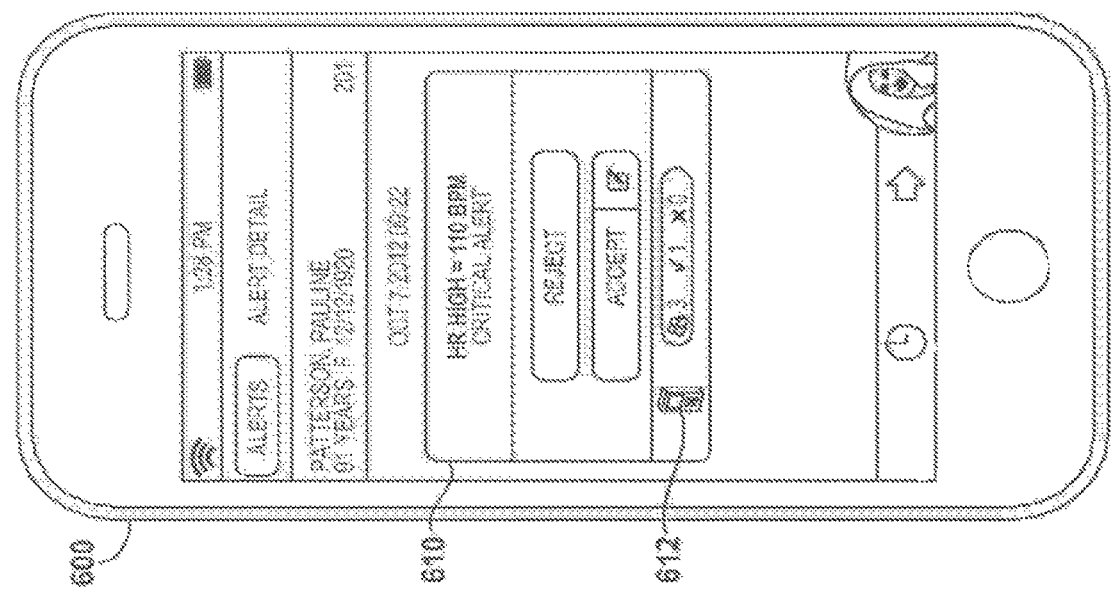
FIG. 6.

ALERT MANAGEMENT UTILIZING MOBILE DEVICES

CROSS-REFERENCE TO RELATED APPLICATIONS

This application is a continuation of U.S. application Ser. No. 16/179,096, filed Nov. 2, 2018, and entitled "Alert Management Utilizing Mobile Devices," which is a continuation of U.S. application Ser. No. 15/873,158, filed Jan. 17, 2018 and entitled "Alert Management Utilizing Mobile Devices," subsequently issued as U.S. Pat. No. 10,121,346, which is a continuation of U.S. application Ser. No. 15/684,563, filed Aug. 23, 2017 and entitled "Alert Management Utilizing Mobile Devices," subsequently issued as U.S. Pat. No. 9,911,300, which is a divisional of U.S. application Ser. No. 15/630,617, filed Jun. 22, 2017 and entitled "Alert Management Utilizing Mobile Devices," subsequently issued as U.S. Pat. No. 9,836,940, which is a continuation of U.S. application Ser. No. 15/392,926, filed Dec. 28, 2016 and entitled "Alert Management Utilizing Mobile Devices," subsequently issued as U.S. Pat. No. 9,805,573, which is a continuation of U.S. application Ser. No. 14/877,808, filed Oct. 7, 2015 and entitled "Alert Management Utilizing Mobile Devices," subsequently issued as U.S. Pat. No. 9,582,978, which is a continuation of U.S. application Ser. No. 13/731,191, filed Dec. 31, 2012 and entitled "Alert Management Utilizing Mobile Devices," subsequently issued as U.S. Pat. No. 9,185,202. The entirety of the aforementioned applications is incorporated by reference herein.

BACKGROUND

Typical nurse management of patient alerts utilizes stationary computer terminals located at, for example, a nursing station associated with a nursing unit. The stationary terminals are manned by unit secretaries who receive alerts or other important information related to patients on the unit. The unit secretary then identifies the caregivers assigned to those patients and may attempt to contact the caregivers through a variety of methods such as electronic paging, calling a patient's room to see if the caregiver is in the room, or overhead paging. Caregivers then either have to call the unit secretary or return to the nursing station to retrieve the alerting information. The result is inefficient communication, unproductive workflows, and time lags between when alerting information is received and when it is acted on by the caregiver.

In those situations where a patient alert is pushed to a caregiver's mobile device, the alert often lacks important patient-contextual information, such as medical values, images, or device readings associated with the alert, that help the caregiver in deciding how to appropriately respond to the alert. The caregiver must then either return to the nursing station to access the information or open up a computer application on the mobile device to access the needed information—both of which consume valuable time resources. Further, though the caregiver may receive an alert, the caregiver is generally not given an opportunity to further interact with the alert. For instance, the alert generally cannot be communicated to another caregiver that can assist in addressing the alert.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for managing patient alerts using mobile devices. A patient alert is received and presented on a caregiver's mobile device; the caregiver is part of the patient's care team. The alert includes patient-identifying information along with the alert identifier and contextual patient data related to the alert. If the alert is a critical alert, the alert must be acknowledged in some manner before the caregiver can resume use of the mobile device. Acknowledgment of the alert may comprise rejecting the alert or accepting the alert. Rejection of the alert by the caregiver causes the alert to be automatically communicated to another caregiver assigned to the patient. Acceptance of the alert by the caregiver enables the caregiver to access members of the patient's care team and to forward the alert on to selected members of the team that can assist the caregiver in addressing the alert.

BRIEF DESCRIPTION OF THE DRAWINGS

Embodiments are described in detail below with reference to the attached drawing figures, wherein:

FIG. 3 is a flow diagram of an exemplary method of accepting and managing patient alerts using a mobile device in accordance with an embodiment of the present invention;

FIG. 4 is a flow diagram of an exemplary method of managing patient alerts when an alert is rejected in accordance with an embodiment of the present invention;

FIG. 6 is a series of exemplary graphical user interfaces illustrating the ability to see trending data related to a patient alert in accordance with an embodiment of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for managing patient alerts using mobile devices. A patient alert is received and presented on a caregiver's mobile device; the caregiver is part of the patient's care team. The alert includes patient-identifying information along with the alert identifier and contextual medical data related to the alert. If the alert is a critical alert, the alert must be acknowledged in some manner before the caregiver can resume use of the mobile device. Acknowledgment of the alert may comprise rejecting the alert or accepting the alert. Rejection of the alert by the caregiver causes the alert to be automatically communicated to another caregiver assigned to the patient. Acceptance of the alert by the caregiver enables the caregiver to access members of the patient's care team and to forward the alert on to selected members of the team that can assist the caregiver in addressing the alert.

Figure 1:
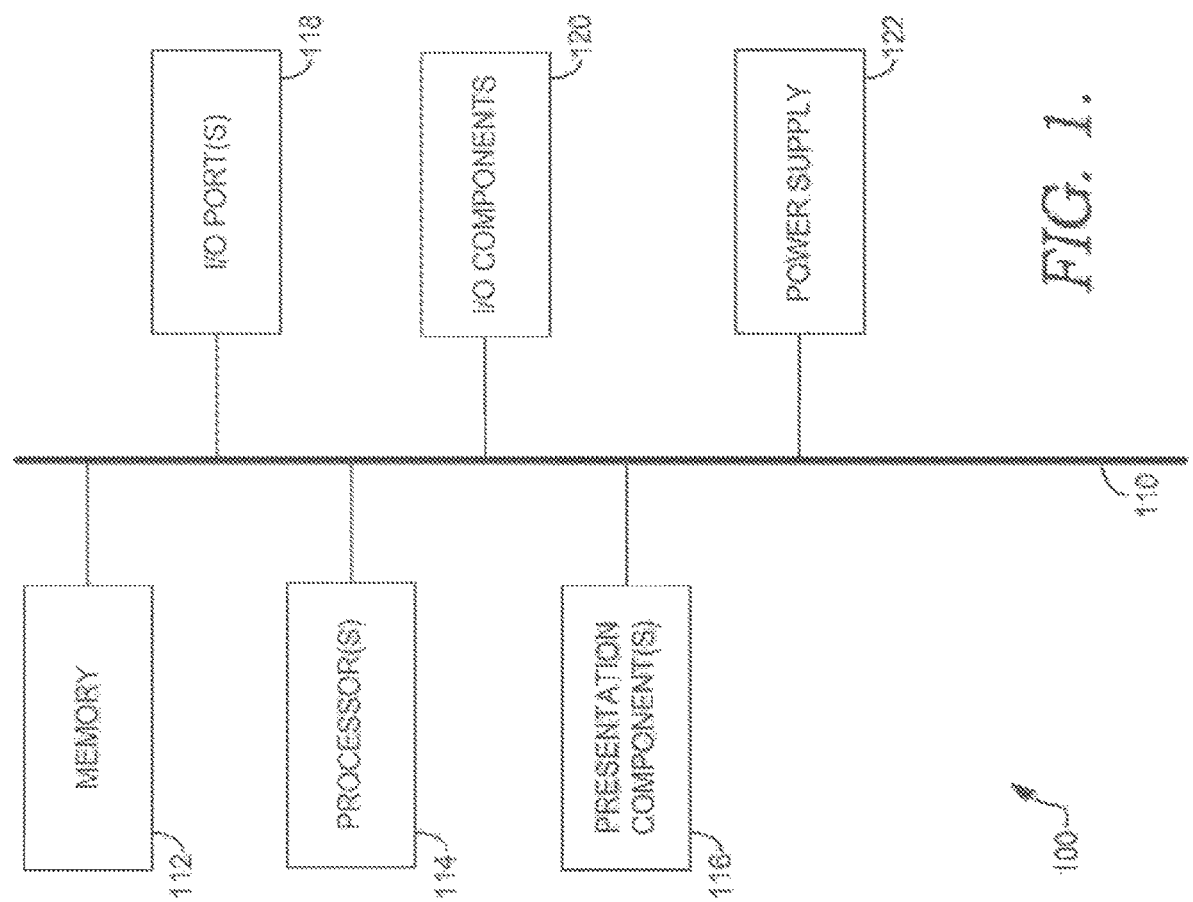
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
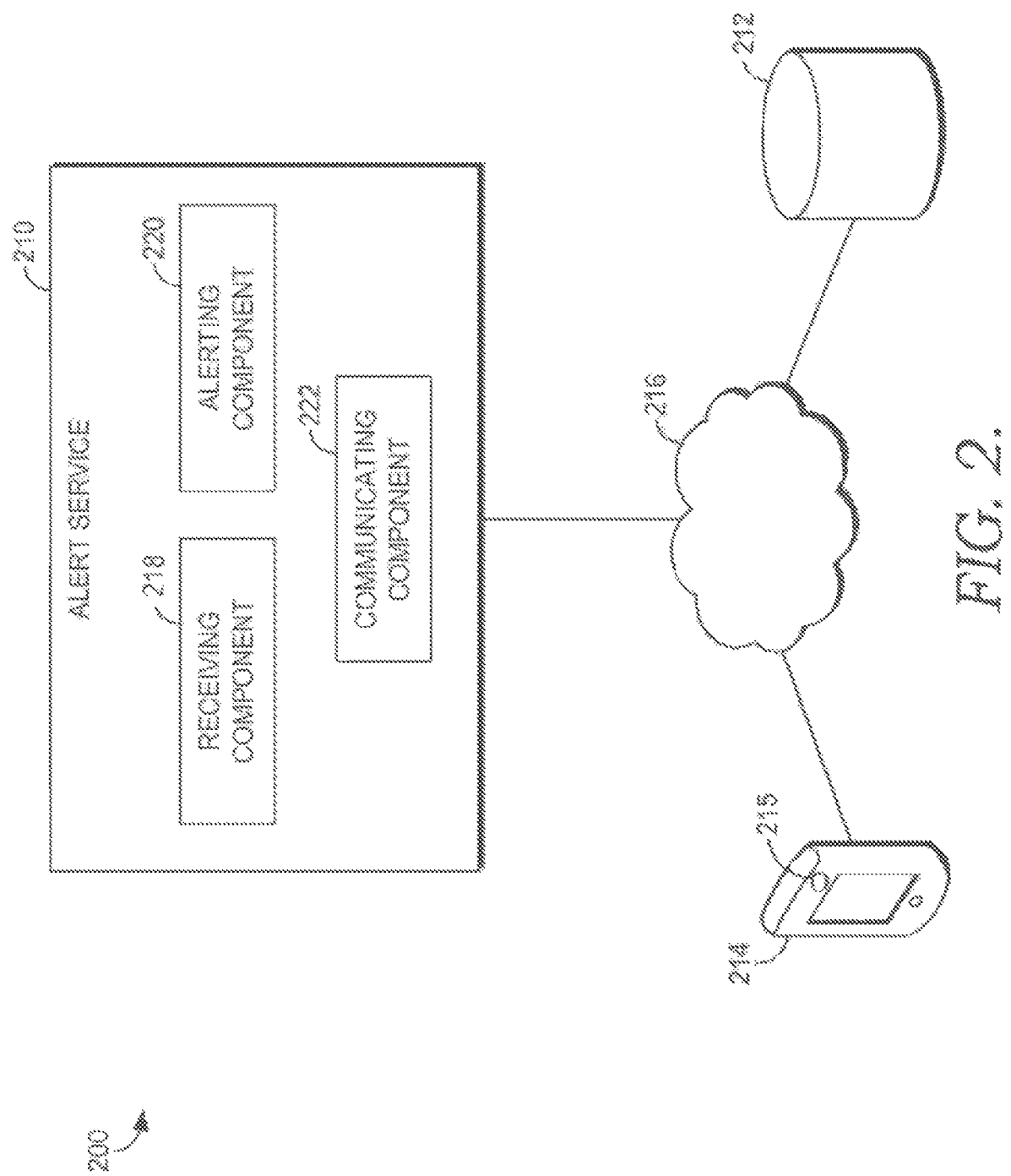
FIG. 2 is a block diagram of an exemplary system for managing patient alerts suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes an alert service 210, a data store 212, and a mobile device 214 all in communication with one another via a network 216. The network 216 may include, without limitation, one or more secure local area networks (LANs) or wide area networks (WANs). The network 216 may be a secure network associated with a facility such as a healthcare facility. The secure network 216 may require that a user log in and be authenticated in order to send and/or receive information over the network 216.

In some embodiments, one or more of the illustrated components/modules may be implemented as stand-alone applications. In other embodiments, one or more of the illustrated components/modules may be integrated directly into the operating system of the alert service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the alert service 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the alert service 210 and/or the mobile device 214. The information stored in association with the data store 212 is configured to be searchable for one or more items of information stored in association therewith. The information stored in association with the data store 212 may comprise general information used by the alert service 210 and/or the mobile device 214.

The data store 212 may store electronic medical records (EMRs) of patients associated with one or more healthcare facilities. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Additionally, the data store 212 may store information concerning decision-support algorithms, reference materials, standards of care, recommendation protocols, alert protocols, and the like. This information may be specific to a healthcare facility, or the information may be promulgated by, for example, nationally-recognized medical organizations or governing bodies. Information stored in the data store 212 may also include staffing assignments (e.g., which caregivers are assigned to care for a patient), and availability information for the different caregivers. For instance, a caregiver who is logged into the network 216 is flagged as available; a caregiver who is logged into the network 216 but who has indicated that he/she is busy is flagged as available but busy; and a caregiver who is not logged into the network 216 is flagged as offline. Staffing and availability information is continually updated. As used throughout this application, the term "caregiver" generally means healthcare workers such as registered nurses, aids, respiratory therapists, physical therapists, occupational therapists, and the like. Caregivers such as these provide the day-to-day care of patients but normally do not have ordering privileges.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the alert service 210, the mobile device 214, and/or any combination thereof.

The mobile device 214 may be any type of wireless-telecommunications device. Such devices may include any type of mobile and portable devices including cellular telephones, personal digital assistants, tablet PCs, smart phones, and the like. The mobile device 214 includes a set of embodied computer-executable instructions 215 that carry out various functional aspects of the invention. In one aspect, the mobile device 214 may be associated with or assigned to a caregiver by the healthcare facility. In another aspect, the mobile device 214 may be owned by the caregiver and registered with the healthcare facility. The mobile device 214 is capable of communicating with other associated or registered mobile devices by utilizing the secure network 216.

As shown, the mobile device 214 includes a display screen. The display screen is configured to display information to the user of the mobile device 214. The information may include communications initiated by and/or received by the mobile device 214, patient alerts, medical data related to the patient alerts, care lists, availability information, and the like. Embodiments are not intended to be limited to visual display but rather may also include audio presentation, combined audio/visual presentation, and the like.

Components of the alert service 210 and the mobile device 214 may include a processing unit, internal system memory, and a suitable system bus for coupling various system components, including one or more data stores for storing information (e.g., files and metadata associated therewith). The alert service 210 and the mobile device 214 typically include, or has access to, a variety of computer-readable media.

The computing system environment 200 is merely exemplary. While the alert service 210 is illustrated as a single unit, it will be appreciated that the alert service 210 is scalable. For example, the alert service 210 may in actuality include a plurality of computing devices in communication with one another. Moreover, the data store 212, or portions thereof, may be included within, for instance, the alert service 210 and the mobile device 214 as a computer-storage medium. The single unit depictions are meant for clarity, not to limit the scope of embodiments in any form.

As shown in FIG. 2, the alert service 210 comprises a receiving component 218, an alerting component 220, and a communicating component 222. In some embodiments, one or more of the components 218, 220, and 222 may be implemented as stand-alone applications. In other embodiments, one or more of the components 218, 220, and 222 may be integrated directly into the operating system of a computing device such as the remote computer 108 of FIG. 1 or the mobile device 214. It will be understood that the components 218, 220, and 222 illustrated in FIG. 2 are exemplary in nature and in number and should not be construed as limiting. Any number of components may be employed to achieve the desired functionality within the scope of embodiments hereof.

The receiving component 218 is configured to receive information related to patient alerts. Such information may include data from medical devices electronically associated with a patient. Such devices are numerous but representative examples may include respirators, pulse oximeters, blood pressure monitors, blood glucose monitors, heart rate/rhythm monitors, input/output monitors, fetal monitors, and the like. Data from medical devices includes values, waveform tracings, images, and the like. The receiving component 218 may also receive patient-identifying information from, for example, the data store 212 along with an alert history for the patient and normal value ranges for the patient.

Continuing, the receiving component 218 is further configured to receive staffing assignments from, for example, the data store 212 or a staffing/scheduling system associated with the healthcare facility caring for the patient. Staffing assignments include caregivers assigned to care for the patient during a specified time frame. Staffing assignments may depend on the patient's medical condition. By way of illustrative example, a patient who is rehabilitating from a serious car accident may be assigned a primary caregiver (e.g., a nurse), a secondary caregiver that cares for the patient when the primary caregiver is busy, a respiratory therapist, a physical therapist, and an occupational therapist.

The receiving component is additionally configured to receive availability information for each of the patient's assigned caregivers. This information may be stored in association with the data store 212 or with the staffing/scheduling system. The availability status for any one caregiver may include the status of available, available but busy, and offline. The status of available occurs when the caregiver is logged in and authenticated to the secure network 216. The status of available but busy occurs when the caregiver is logged in but has marked himself as busy using, for example, the mobile device 214. The status of offline occurs when the caregiver is logged off of the network 216.

The receiving component 218 also receives location information for the caregivers, the patient, and devices associated with the patient from, for example, a real-time location service associated with the healthcare facility. Such services use a variety of methods known in the art to track location information including radio-frequency identification (RFId) tags and sensors located throughout the healthcare facility.

The receiving component additionally receives information from the nurse call system of the healthcare facility. The nurse call system enables communication between the patient and caregivers utilizing a number of different devices such as a pillow speaker. Some systems enable the patient to enter information concerning the nurse call before it is transmitted to the nurse. For instance, the patient may input that he/she would like ice chips, or that he/she is having difficulty breathing or is in pain.

The alerting component 220 is configured to use the information received by the receiving component 218 to generate alerts. The alerting component 220 may utilize the information in association with clinical guidelines, alerting protocols, and/or standardized recommendations to determine if and what type of alert should be generated. The alerts can be broadly categorized as critical alerts and non-critical alerts. Critical alerts can be generally defined as those alerts that can have a negative impact on a patient's health if not addressed in a timely manner. On the other hand, non-critical alerts can be generally defined as those alerts that do not negatively impact the patient's health if not addressed in a timely manner. Some representative examples of critical alerts may include a heart arrhythmia, low oxygen saturation, low respiratory rate, elevated blood pressure, presence of sepsis indicators, and the like. Some representative examples of non-critical alerts include patient requests for ice chips or toiletry assistance, lab values or device readings that are slightly outside of the normal range, indication that a new patient order has been received, and the like.

The communicating component 222 is configured to communicate patient alerting information to the mobile device 214. The alerting information includes an alert identifier, status indicators related to the alert, patient-identifying information, lab values related to the alert, medication orders related to the alert, and device readings related to the alert. In one aspect, lab values, medication orders, and device readings (e.g., waveform tracings, values, and/or images) are related to the alert if they triggered the alert. The waveform tracings, values, and/or images may be time-stamped and may include a predefined time period before the alert was triggered, a time period corresponding to the alert trigger, as well as a predefined time period after the alert was triggered. The mobile device 214 then presents this information to the caregiver as more fully described below.

In one aspect, the communicating component 222 communicates the patient's alerting information initially to the mobile device associated with the patient's primary caregiver. If the primary caregiver rejects the alert, the communicating component 222 may next communicate the patient's alerting information to the mobile device associated with the patient's secondary caregiver. If the secondary caregiver rejects the alert, the communicating component 222 may communicate the patient's alerting information to the mobile device associated with the charge nurse of the patient's unit. If the charge nurse rejects the alert, the communicating component 222 may communicate the alert to mobile devices associated with every member of the patient's care team.

In another aspect, the communicating component 222 determines the caregiver role best suited to initially address the particular patient alert, and communicates the alerting information to mobile devices associated with caregivers in that role. By way of illustrative example, a patient alert indicates that a patient's oxygen saturation levels have dropped below recommended ranges. The communicating component 222 determines that a respiratory therapist would be suited to address this alert and communicates the alerting information to the mobile device associated with the respiratory therapist. The alerting information may at the same time be communicated to the mobile device associated with the patient's primary caregiver.

In yet another aspect, the communicating component 222 determines caregivers in close proximity to the patient that is the subject of the alert, determines if the role of those caregivers that are located close to the patient is suited to meet the particular patient alert, and, if so, communicates the initial alert to those caregivers. The alerting information may at the same time be communicated to the mobile device associated with the patient's primary caregiver. Any and all of such aspects, and any combination thereof, are contemplated as being within the scope of the invention.

The communicating component 222 is further configured to receive communications from the mobile device 214. Such communications may comprise notifications that the alert has been acknowledged and accepted by the recipient. This information is time-stamped and may be stored in association with the patient's electronic medical record. Another communication may comprise a notification that the alert was rejected by the recipient. Other communications from the mobile device may include indicators that the recipient of the alert has communicated the alert to other members of the care team. The indicators may include the identities of the additional recipients, whether the additional recipients acknowledged receipt of the alert, and a time the alert was forwarded. Communications from the mobile device 214 may additionally include requests for more information.

Turning now to FIG. 3, a flow diagram is depicted of an exemplary method 300 of managing patient alerts on a mobile device. At a step 310, a first mobile device such as the mobile device 214 of FIG. 2 receives an alert related to a patient being cared for at a healthcare facility. In one aspect, the alert may be received from a communicating component of an alert service such as the communicating component 222 of the alert service 210. In another aspect, the alert may have been communicated by another mobile device. The first mobile device, in one aspect, has previously been registered, associated with or assigned to a member of the patient's care team such as the patient's primary and/or secondary caregiver. The receipt of the alert may be accompanied by an auditory sound or a physical action such as a vibration to alert the caregiver that an alert has been received.

At a step 312, the alert is presented on the first mobile device. If the alert is a critical alert, the alert is configured to interrupt or supersede any applications that are currently running on the first mobile device. For instance, the alert may be presented as a pop-up that overlies other content on the mobile device. The caregiver cannot access other functionalities associated with the first mobile device until the caregiver acknowledges the alert by either accepting or rejecting the alert. This helps to ensure that critical alerts are addressed in a timely manner by the caregiver.

The alert presented on the first mobile device includes patient-identifying information such as the patient's name, room location, and the patient's date of birth. The alert also includes an alert identifier and an alert status. The alert identifier conveys to the caregiver the nature of the alert. For instance, identifiers may include phrases such as "ADE" for an adverse drug event, "HR high" to indicate the heart rate is outside of the normal range, "Low SPO2" to indicate low blood oxygen saturation, "Diastolic High" to indicate that diastolic blood pressure is high, and "SEPSIS: SIRS Criteria Met" to indicate that the patient is possibly becoming septic. These are just a few representative examples provided for illustration purposes only. Any identifier that provides a brief description of the nature of the alert is contemplated as being within the scope of the invention. The alert status may be indicated by textual phrases such as "Critical Alert," color coding, flashing images, and the like.

The alert may also comprise a short summary of lab values, medications, images, or device readings that are pertinent to the alert. In one aspect, the values, medications, images, or device readings that triggered the alert are presented in the short summary. The device readings may include a snippet of a waveform tracing or trending graph that was taken by the monitoring device at the time the alert was triggered. The snippet may be time-stamped and may include a time period before the alert, a time period during the alert, and a time period after the alert was triggered. For instance, an elevated heart rate alert may include the detected heart rate along with a snippet of a heart rate rhythm waveform tracing captured around the time the alert was triggered. This important patient-contextual information is presented in association with the alert to assist the caregiver in making a quick assessment of the alert situation. The alert may also include options for accepting the alert or rejecting the alert. Exemplary options include an accept icon, button or bar, and a reject icon, button or bar.

At a step 314, an acceptance of the alert by the caregiver is received by the first mobile device. The caregiver may accept the alert by tapping, swiping, or otherwise selecting, for example, the acceptance icon, bar, or button. Once selected, at a step 316, a list of one or more additional caregivers assigned to the patient is presented on the first mobile device. The list may include the names of the other caregivers, a thumbnail picture of the caregiver, roles associated with each of the caregivers, locations of the caregivers, and/or the availability status of the caregivers. The list may be ordered based on caregiver role such that caregivers most suited to meet the alert needs are presented at the top of the list. The list may also be ordered based on proximity to the patient location. Thus the recipient of the alert can quickly assess which caregivers are located closest to the patient. The list may additionally be ordered based on a combination of user role and proximity to the patient. Other ways of ordering the list include alphabetical order and availability status. Any and all such aspects, and any combination thereof, are contemplated as being within the scope of the invention.

Caregivers on the list are associated with an availability status indicator. These indicators may indicate that the caregiver is available, available but busy, or is not currently logged into the network. Availability status indicators may include color-coded indicators such as green for available, white for offline, and red for available but busy. Other ways of indicating availability status may include textual descriptions, and other types of visual indicators known in the art.

At a step 316, a selection of one or more additional caregivers is received by the first mobile device. This may occur, for example, when the recipient of the alert selects a caregiver by tapping or swiping on the caregiver's information. Once selected, at a step 318, the first mobile device communicates the alert to at least a second mobile device associated with the selected caregiver. In one aspect, the original recipient of the alert can simply call a caregiver on the list. In another aspect, the alert is communicated as a short message service (SMS) message or a multimedia message service (MMS) message. The alert that is communicated to the selected caregiver includes the patient-identifying information, the alert identifier, the alert status, and lab values, device readings, medication orders, images, and/or trending graphs associated with the alert. Further, when the alert is communicated as a SMS message or a MMS message, the original recipient may optionally enter a textual message in association with the alert. In one aspect, the original recipient receives a notification when the selected caregiver acknowledges the alert.

Turning now to FIG. 4, a flow diagram is depicted illustrating an exemplary method 400 of managing patient alerts using a mobile device. At a step 410, a patient alert is received on a first mobile device such as the mobile device 214 of FIG. 2. The patient alert may be communicated to the first mobile device by an alert service such as the alert service 210 of FIG. 2. The first mobile device is associated with or assigned to a member of the patient's care team, such as the patient's primary or secondary caregiver.

At a step 412, if the alert is a critical alert, the alert is presented on the first mobile device such that it interrupts or supersedes any currently running applications on the mobile device. The alert may be received and presented in association with an audible sound, and/or a physical action such as a vibration. If the alert is a non-critical alert, the recipient may be notified of the alert via a pop-up message, or the alert may be briefly presented. Non-critical alerts generally do not supersede currently running applications on the mobile device. As discussed above, the critical alert includes patient-identifying information, the alert identifier, the alert status, lab values, device readings, images, trending graphs, and/or waveform tracings that are related to the alert, and options for accepting or rejecting the alert.

At a step 414, a rejection of the alert is received by the first mobile device. In one aspect, the rejection may be initiated by the alert recipient affirmatively selecting a rejection button, icon, bar, or the like. The recipient caregiver may reject the alert if he or she is currently busy and cannot address the alert in a timely manner. At a step 416, the alert is automatically communicated to a second mobile device associated with at least a second caregiver assigned to care for the patient. The selection of the second caregiver may be based on an alerting protocol associated with, for example, a data store such as the data store 212 of FIG. 2. The second caregiver may, in one aspect, comprise the secondary caregiver assigned to the patient. The alert may automatically be communicated to more than one additional caregiver.

The alert that is automatically communicated to the second mobile device at step 416 is substantially identical to the original alert. For example, it includes patient-identifying information, alert name, alert status, lab values, device readings, images, waveform tracings, and/or trending graphs, along with options to accept or reject the alert. The caregiver associated with the second mobile device can accept the alert which initiates the steps outlined above with respect to FIG. 3. Alternatively, the caregiver associated with the second mobile device can reject the alert which initiates the steps outlined above with respect to FIG. 4.

In one aspect, failure by the alert recipient to address the alert within a predetermined period of time causes the alert to be automatically communicated to additional mobile devices such as mobile devices associated with the patient's secondary caregiver, the charge nurse, or other caregivers on the patient's care team. The predetermined period of time may range from one minute up to five minutes and may be dependent on the criticality of the alert.

Figure 10:
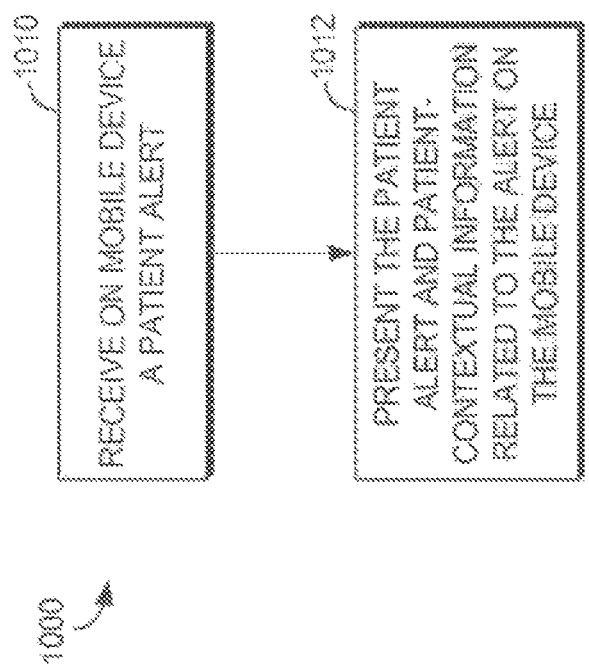
FIG. 10 is a flow diagram of an exemplary method of receiving an alert that includes patient-contextual information related to the alert using a mobile device in accordance with an embodiment of the present invention.

FIG. 10 is a flow diagram of an exemplary method 1000 of receiving patient-contextual information related to an alert on a mobile device. At a step 1010, a patient alert is received on a first mobile device associated with a first caregiver caring for the patient. In one aspect, the first caregiver is the patient's primary caregiver. At a step 1012, the patient alert is presented on the first mobile device. The patient alert may include patient-identifying information such as patient name, age, gender, and room location. The alert may also include one or more items of patient information relevant to the alert. In one aspect, patient information is relevant to the alert if it triggered the alert. For example, a lab value that is outside the normal range may trigger the alert, and the lab value would be presented on the mobile device. Patient information relevant to the alert may include lab values, medication orders, and/or device readings. Device readings, in turn, may include waveform tracings, trending graphs, images, and the like.

Figure 5:
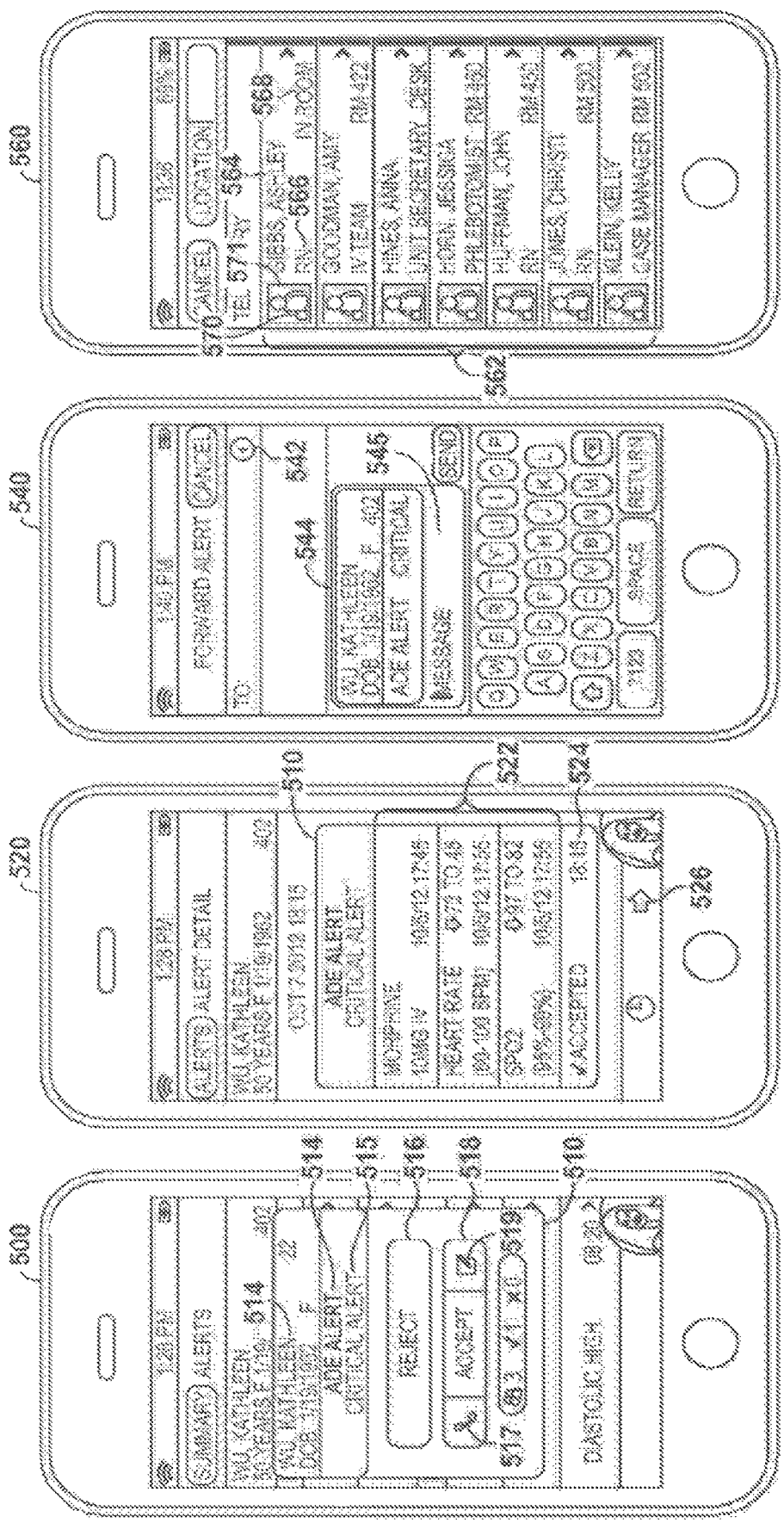
FIG. 5 is a series of exemplary graphical user interfaces illustrating the acceptance and management of patient alerts in accordance with an embodiment of the present invention.

Turning now to FIG. 5, a series of exemplary graphical user interfaces (GUIs) 500, 520, 540, and 560 are depicted; the series of GUIs illustrate how patient alerts are managed using a mobile device such as the mobile device 214 of FIG. 2. GUI 500 is the first in the series and depicts a critical alert 510 presented on the mobile device. The alert 510 overlays existing content of the mobile device and is displayed until acted on by the recipient of the alert 510. The alert 510 includes a patient identification area 512 that presents information such as patient name, patient identification number, room number, date of birth, and the like. The alert 510 also includes an alert identifier 514 and an alert status 515. The alert identifier 514 (e.g., "ADE ALERT") provides a brief description of the alert, and the alert status 515 indicates that the alert is critical. In one aspect, only critical alerts are presented utilizing the methods described above. The alert 510 additionally includes a selectable "reject" bar 516 and a selectable "accept" bar 518. Although bars are depicted, other selectable options are contemplated such as icons or buttons. The accept bar 518 has a call option 517 and a message option 519. In one aspect, when the call option 517 is selected, the recipient is automatically presented with a call contact list comprising members of the patient care team. The call contact list includes names of the caregivers, pictures of the caregivers, availability indicators, location information, user role, and the like. In another aspect, when the call option 517 is selected, a call to the patient room is automatically placed so that the caregiver can speak with the patient. When the message option 519 is selected, the recipient is presented with a messaging GUI as shown in the GUI 540.

GUI 520 depicts the presentation of additional information 522 associated with the alert 510. The additional information 522 may be presented when the alert recipient selects, for example, the alert identifier 514 or some other portion of the alert 510. The additional information 522 may include such items as medications, lab values, device readings, and the like. Medication information may include the dosage amount, the dosage route, and the day and time when the medication was last administered. Lab value information and device reading information may include a normal range, a previous value, a current value, a date and time when obtained, and an indicator that indicates whether the current value is greater or lesser than the previous value. Each of the items of information 522 provides patient context to the alert 510 and assist the alert recipient to make an informed decision regarding how to effectively address the alert. The GUI 520 also includes an acceptance area 524 that indicates the time the alert 510 was accepted by the recipient.

The GUI 540 may be presented when the recipient selects the message option 519, or when the recipient advances to the next screen utilizing a forward page icon as shown at item 526 on GUI 520. The GUI 540 includes an alert depiction 544 that includes patient-identifying information, the alert identifier, and the alert status. The alert depiction 544 also includes a message area 545 where the recipient can input a message. The GUI 540 also includes a selectable icon 542, that, when selected, initiates the presentation of a list of caregivers that are on the patient's care team.

GUI 560 depicts the care team list 562 that is presented upon selection of the selectable icon 542 of GUI 540. The care team list 562 includes all caregivers that are currently assigned to the patient. Using caregiver Ashley Gibbs 564 as an illustrative example, information presented in association with Ashley Gibbs 564 includes a picture 571, a role 566 (e.g., "RN"), a location 568 (e.g., "In Room"), and an availability indicator 570. The availability indicator 570 may be color coded to indicate availability. For example, the indicator 570 may be colored green if the caregiver 564 is available, red if the caregiver 564 is available but busy, and white if the caregiver 564 is offline. Further, for those users who are color-blind, the color coded indicators may be placed in different locations so the user can distinguish between, for example, a red indicator and a green indicator. For example, green indicators may be presented on the right side of the screen, and red indicators may be presented on the left side of the screen.

The list 562 may be categorized by user role, availability status, and/or proximity to the patient. Although not shown, the alert recipient can select by, for example, swiping, tapping, or using other gestures known in the art, one or more caregivers on the list and communicate the alert to the selected caregivers. The alert information 522 is communicated with the alert so that the selected caregivers can quickly access the needed information.

FIG. 6 depicts a series of two exemplary GUIs 600 and 620 illustrating the presentation of waveform tracings associated with a patient alert. GUI 600 includes an alert 610 that includes the information already outlined above with respect to, for example, the alert 510 of FIG. 5. The GUI 600 further includes a display icon 612. Selection of the display icon 612 initiates the presentation of GUI 620. The GUI 620 includes the alert 610 along with a waveform tracing 622. The waveform tracing 622 is captured and time-stamped by the patient's device at the time the alert was triggered and may include segments of time before and after the alert was triggered to provide additional context for the waveform tracing. Although a waveform tracing is shown, it is also contemplated that an image captured by a camera or a monitoring device may be presented. For instance, a caregiver may take a picture of a patient's wound and this image may be included with the alert 610. The waveform tracing 622, and/or image, is used by the alert recipient to select other caregivers to notify so that the alert can be properly addressed.

Figure 7:
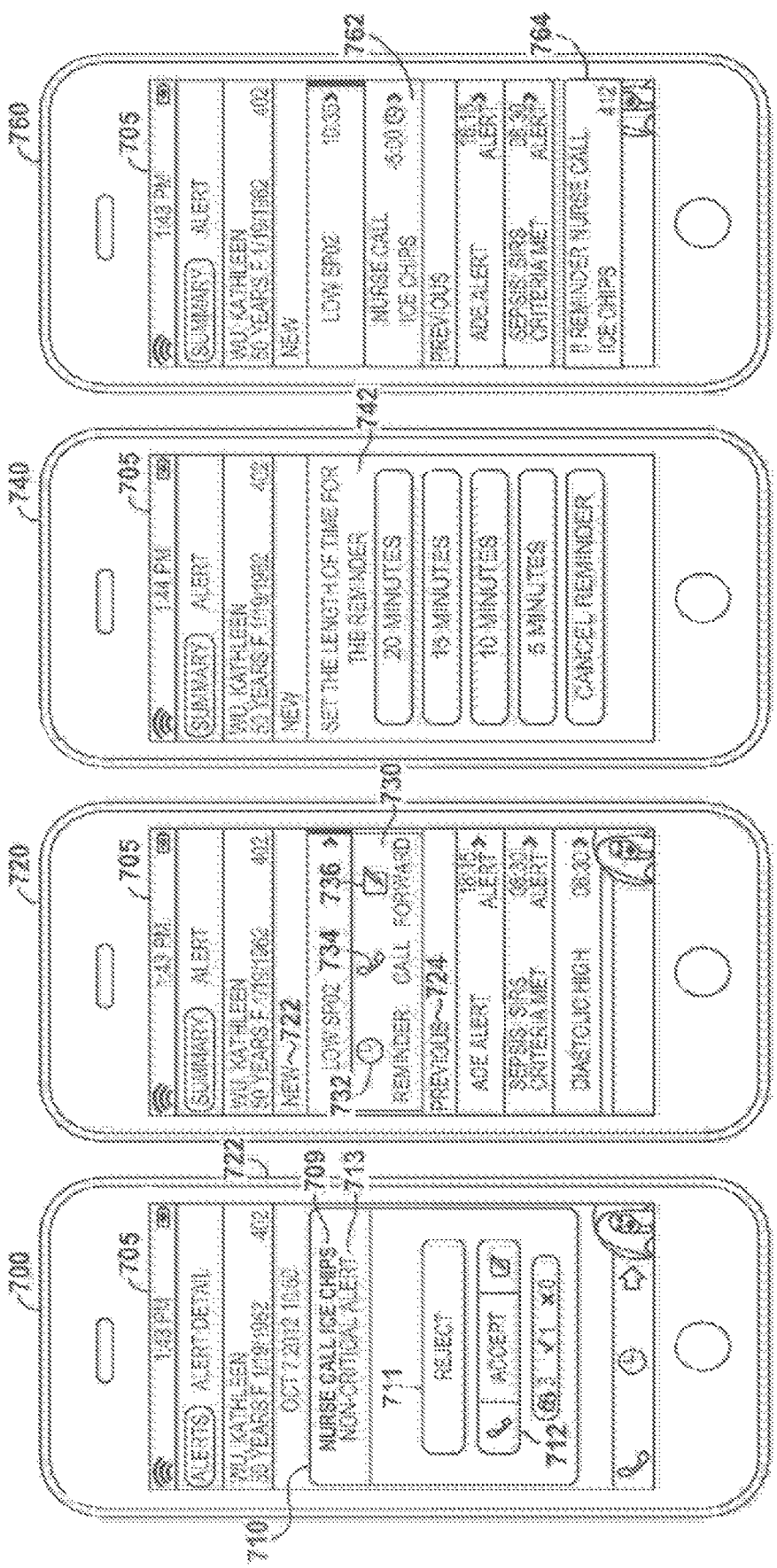
FIG. 7 is a series of exemplary graphical user interfaces illustrating the ability to utilize reminders with non-critical alerts in accordance with an embodiment of the present invention.

FIG. 7 depicts a series of exemplary GUIs 700, 720, 740, and 760 that illustrate how reminders can be generated for non-critical alerts. GUI 700 depicts an alert review screen 705 on which a non-critical alert 710 has been selected. The alert review screen 705 may be accessed from a general menu (not shown). Non-critical alerts differ from critical alerts in that they generally do not supersede any currently running applications. Non-critical alerts may be presented as a pop-up that persists for a short period of time before fading. The pop-up may be dismissed by the user by, for example, selecting a different area of the display screen. Non-critical alerts may also be presented to the caregiver on the mobile device as a notification message, and the caregiver can review the alert at his/her discretion. Non-critical alerts differ from critical alerts in that reminders may be set for non-critical alerts. By contrast, because of the time-sensitive nature of critical alerts, reminders cannot be set for critical alerts.

The non-critical alert 710 includes an alert identifier 709, an alert status 713, a reject option 711, and an accept option 712. If the caregiver chooses to accept the non-critical alert 710 by tapping, swiping, or otherwise selecting, a set of options 730 is presented as shown on the GUI 720. The GUI 720 includes the alert review screen 705. The set of options 730 includes a reminder option 732 to set a reminder, a call option 734 to call a caregiver or to call the patient's room, and a message option 736 to message a caregiver on the patient's care team. The alert review screen 705 in the GUI 720 also depicts new patient alerts 722 and previous patient alerts 724; the new patient alerts 722 and the previous patient alerts 724 include both critical and non-critical alerts. Each alert includes an alert identifier, and a time when the alert was triggered.

GUI 740 depicts the alert review screen 705 and a reminder screen 742 that is initiated upon a user selection of the reminder option 732 in the set of options 730 of GUI 720. The reminder screen 742 enables the caregiver to select from a range of reminder times or to cancel the reminder. Reminder times may include 5 minutes, 10 minutes, 15 minutes, and 20 minutes.

GUI 760 depicts the alert review screen 705 after a reminder time has been selected. As shown by alert 762, the non-critical alert for ice chips is now associated with a reminder time of 5 minutes. Further, area 764 is a visual indicator that one or more reminders have been initiated for non-critical alerts. The area 764 includes the names of alerts that have been associated with a reminder, as well as an indicator to draw the user's attention to the area 764 (e.g., an exclamation point).

Figure 8:
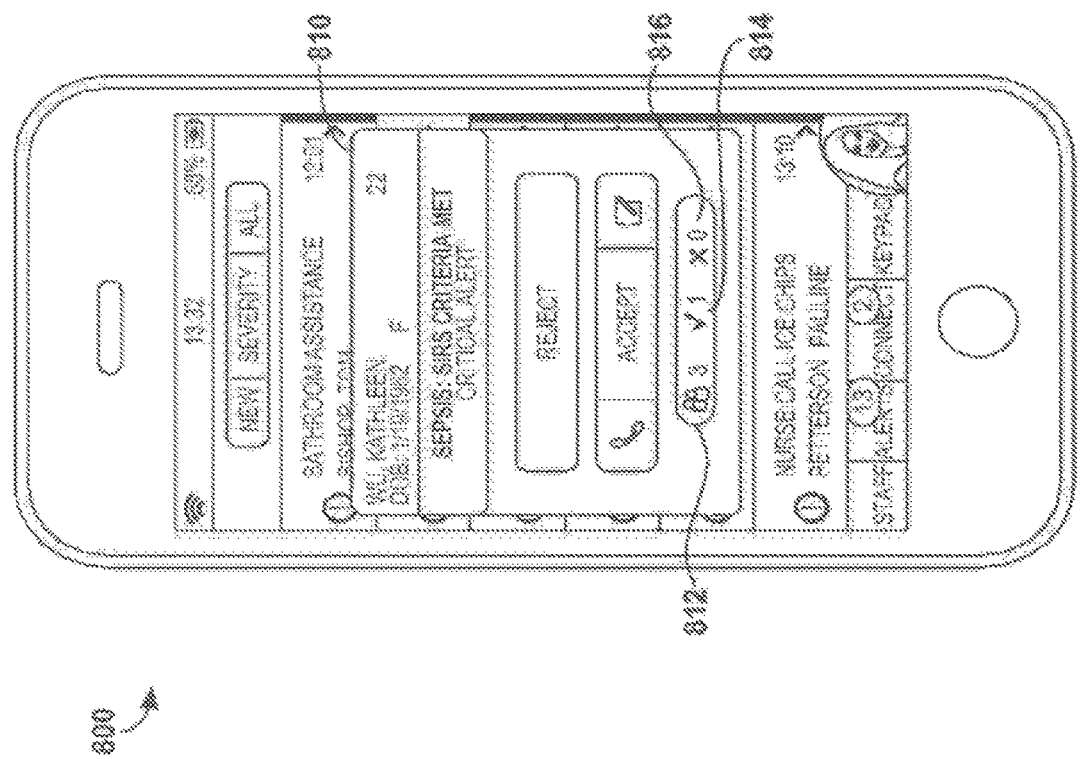
FIG. 8 is an exemplary graphical user interface illustrating the additional information presented with an alert in accordance with an embodiment of the present invention.

FIG. 8 depicts an exemplary GUI 800 illustrating additional information that may be associated with a critical alert. The GUI 800 includes a critical alert 810. The critical alert 810 includes the same information as outlined above with respect to the alert 510 of FIG. 5. The alert 810 may further include a number of people that were sent the alert as indicated by element 812. Thus, in this case, the alert 810 was communicated to three caregivers associated with the patient. The alert 810 also includes an indication of the number of caregivers who accepted the alert 810; this is shown by element 814. In this case, one caregiver has accepted the alert. Additionally, the alert 810 includes an indication of the number of caregivers who have rejected the alert 810 (in this case, zero caregivers have rejected the alert 810).

Figure 9:
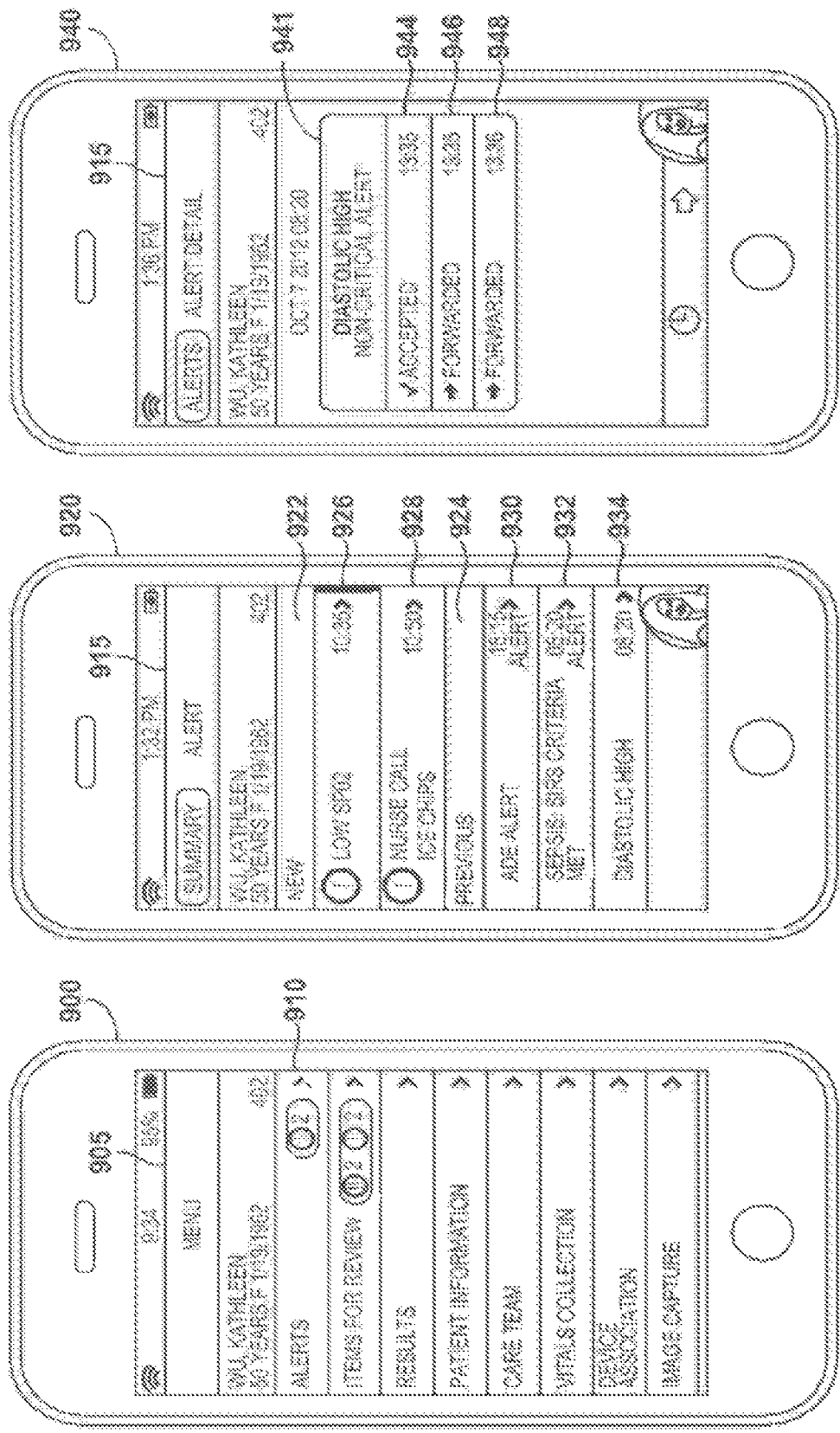
FIG. 9 is a series of exemplary graphical user interfaces illustrating the ability of a caregiver to review an alert history in accordance with an embodiment of the present invention.

FIG. 9 depicts a series of exemplary GUIs 900, 920, and 940 that illustrate the ability of a caregiver to review an alert history for a patient. The GUI 900 depicts a general menu screen 905. The general menu screen includes an alerts review 910 bar by which the caregiver can review alerts related to the patient (e.g., patient Kathleen Wu). Upon selection of the alerts review bar 910, the user is taken to an alerts review screen 915 that is similar to the alerts review screen 705 of FIG. 7. The alerts review screen 915 includes a new alert area 922 and a previous alert area 924 similar to the new alert area 722 and the previous alert area 724 of FIG. 7. The new alert area 922 includes both a critical alert 926 and a non-critical alert 928. The previous alert area 924 includes three critical alerts 930, 932, and 934. Upon selection of an alert, such as the alert 934, an alert detail screen is presented as shown by alert detail screen 941 of the GUI 940.

The GUI 940 includes the alert review screen 915 and the alert detail screen 941. The alert detail screen 941 includes the alert identifier and the alert status. The alert detail screen 941 further includes a notification 944 that the alert 934 was accepted and the time it was accepted. Additionally, it includes two forwarding indications 946 and 948 that indicate that the alert 934 was forwarded twice and the times when the alert 934 was forwarded.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computing hardware device having computer-executable instructions embodied thereon that, when executed, provide a method for managing patient alerts, the method comprising:
   receiving, on the computing hardware device, an alert related to a patient, the computing hardware device associated with a first caregiver assigned to the patient;
   presenting the alert via the computing hardware device, wherein the alert comprises selectable response options, wherein the selectable response options comprise at least a reject option;
   receiving, at the computing hardware device, a selection of at least one of the selectable response options; and
   executing a functionality corresponding to the at least one of the selectable response options selected at the computing hardware device.

2. The computing hardware device of claim 1, wherein the method further comprises providing an availability status of one or more additional caregivers.

3. The computing hardware device of claim 1, wherein the multiple selectable response options comprises at least an accept option.

4. The computing hardware device of claim 3, wherein the functionality corresponding to the at least one of the selectable response options selected at the computing hardware device is an acceptance of the alert.

5. The computing hardware device of claim 1, wherein the alert comprises an indication of an alert level.

6. The computing hardware device of claim 5, wherein the alert level comprises a critical alert or a noncritical alert.

7. The computing hardware device of claim 1, wherein the alert is a pop-up message.

8. The computing hardware device of claim 7, wherein the pop-up message overlies other user interface elements of the computing hardware device.

9. A computing hardware device having computer-executable instructions embodied thereon that, when executed, provide a method for managing patient alerts, the method comprising:
   receiving, on the computing hardware device, an alert related to a patient, the computing hardware device associated with a first caregiver assigned to the patient;
   determining one or more additional caregivers;
   presenting an alert response interface via the computing hardware device, wherein the alert response interface comprises multiple selectable response options, wherein the multiple selectable response options comprises at least a reject option; and
   receiving, at the computing hardware device, a selection of at least one of the selectable response options.

10. The computing hardware device of claim 9, wherein the method further comprises providing an availability status of one or more additional caregivers.

11. The computing hardware device of claim 9, wherein the multiple selectable response options further comprises at least an accept option.

12. The computing hardware device of claim 9, wherein the multiple selectable response options further comprises a messaging option, wherein selection of the messaging option initiates a message screen.

13. The computing hardware device of claim 9, wherein the functionality corresponding to the at least one of the selectable response options selected at the computing hardware device is an acceptance of the alert.

14. The computing hardware device of claim 9, wherein the alert comprises an indication of an alert level.

15. The computing hardware device of claim 14, wherein the alert level comprises a critical alert or a noncritical alert.

16. The computing hardware device of claim 9, wherein the alert is a pop-up message.

17. The computing hardware device of claim 16, wherein the pop-up message overlies other user interface elements of the computing hardware device.

18. A computer-implemented method, the method comprising:
- receiving, on the computing hardware device, an alert related to a patient, the computing hardware device associated with a first caregiver assigned to the patient;
- determining one or more additional caregivers;
- presenting an alert response interface via the computing hardware device, wherein the alert response interface comprises multiple selectable response options, wherein the multiple selectable response options comprises at least a reject option and an accept option; and
- receiving, at the computing hardware device, a selection of at least one of the selectable response options.

19. The method of claim 18, wherein the alert is a pop-up message.

20. The method of claim 18, wherein the multiple selectable response options further comprises a messaging option, wherein selection of the messaging option initiates a message screen.

* * * * *